United States Patent
Jo et al.

(10) Patent No.: US 7,890,157 B2
(45) Date of Patent: Feb. 15, 2011

(54) METHOD FOR FLUORESCENCE LIFETIME IMAGING MICROSCOPY AND SPECTROSCOPY

(75) Inventors: Javier A. Jo, College Station, TX (US); Laura Marcu, Davis, CA (US); Qiyin Fang, Beverly Hills, CA (US); Thanassis Papaioannou, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 924 days.

(21) Appl. No.: 10/567,248

(22) PCT Filed: Aug. 19, 2004

(86) PCT No.: PCT/US2004/026759
§ 371 (c)(1),
(2), (4) Date: Dec. 13, 2006

(87) PCT Pub. No.: WO2005/019800
PCT Pub. Date: Mar. 3, 2005

(65) Prior Publication Data
US 2007/0197894 A1    Aug. 23, 2007

Related U.S. Application Data

(60) Provisional application No. 60/496,316, filed on Aug. 19, 2003.

(51) Int. Cl.
*A61B 6/00* (2006.01)
*G01N 21/64* (2006.01)
*G01N 31/00* (2006.01)

(52) U.S. Cl. .................... 600/473; 600/476; 422/82.08; 702/28

(58) Field of Classification Search .................. 600/407
See application file for complete search history.

(56) References Cited

U.S. PATENT DOCUMENTS

| 4,937,457 A | 6/1990 | Mitchell |
| 5,196,709 A | 3/1993 | Berndt |
| 6,272,376 B1* | 8/2001 | Marcu et al. ................. 600/477 |
| 2003/0136921 A1* | 7/2003 | Reel ......................... 250/458.1 |

FOREIGN PATENT DOCUMENTS

EP    0442295    8/1991

(Continued)

OTHER PUBLICATIONS

Maarek et al., Time-resolved Fluorescence Spectra of Arterial Fluorescent Compounds: Reconstruction with the Laguerre Expansion Technique, 2000, Photochemistry and Photobiology, 71(2), 178-187.*

(Continued)

*Primary Examiner*—Eric F Winakur
*Assistant Examiner*—Hien Nguyen
(74) *Attorney, Agent, or Firm*—Seth D. Levy; Davis Wright Tremaine LLP

(57) ABSTRACT

A method and system for analysis of fluorescence emission spectroscopy data and fluorescence lifetime imaging microscopy data are described. A unique Laguerre expansion can be found for fluorescence intensity decays of arbitrary form with convergence to a correct solution faster than with conventional methods. The Laguerre expansion technique includes expansion coefficients highly correlated with intrinsic fluorescence lifetimes, allowing direct characterization of fluorescence dynamics. For complex systems, conventional analysis of fluorescence intensity decay in terms of discrete exponential components can not readily provide a true representation of underlying fluorescence dynamics. Utilizing the Laguerre expansion technique, an alternative non-parametric method for analysis of time-resolved fluorescence data from various systems is described, facilitating characterization and discrimination of a sample. An ultra-fast method for analysis of fluorescence lifetime imaging is also described, facilitating real-time analysis of compositional and functional changes in samples, at a microscopic or macroscopic level.

9 Claims, 9 Drawing Sheets

FOREIGN PATENT DOCUMENTS

| | | |
|---|---|---|
| WO | WO9009637 | 8/1990 |
| WO | WO0008443 | 2/2000 |
| WO | 2005/019800 A3 | 3/2005 |

PUBLICATIONS

Jean-Michel Maarek et al, "Time-resolved Fluorescence Spectra of Arterial Fluorescent Compounds; Reconstruction with the Laguerre Expansion Technique" Photochemistry and Photobiology, vol. 71, No. 2, 2000, pp. 178-187.

J.A. Jo et al, "Nonparametric Analysis of Time-Resolved Fluorescence Data Based on the Laguerre Expansion Technique" Proceedings of the 25th Annual International Conference of the IEEE Engineering in Medicine and biology Society, Sep. 17, 2003; pp. 1015-1018; vol. 2.

Javier A. Jo, et al; "Laguerre Nonparametric De-convolution Technique of Time-Resolved Fluorescence Data; Application to the Prediction of Concentrations in a Mixture of Biochemical Components" Conference; Jul. 21, 2004; Proc. SPIE, vol. 5326.

Javier A. Jo, et al; "Fast Model-Free De-convolution of Fluorescence Decay for Analysis of Biological Systems"; Jul. 12, 2004; J. Biomed. Opt., vol. 9, No. 4.

Qiyin Fang, et al., "Time-Domain laser-Induced Fluorescence Spectroscopy Apparatus for Clinical Diagnostics"; Feb. 1, 2004; Rev. Sci. Instrum., vol. 75, No. 1 pp. 151-162.

Jan Siegel et al; "Studying Biological Tissue with Fluorescence Lifetime Imaging; Microscopy, Endoscopy, and Complex Decay Profiles"; Jun. 1, 2003; Applied Optics, vol. 42 pp. 2995-3004.

Rolinsky O J, et al; "A New Approach to Fluorescence Lifetime Sending Based on Molecular Distributions"; May 1, 2033; Proceedings of Spie, vol. 4252, pp. 1-11.

Search Report dated Sep. 25, 2008 for European patent application No. 04781453.8 (filed Aug. 19, 2004), 5 pages.

Examination Report dated Dec. 15, 2008 for European patent application No. 04781453.8 (filed Aug. 19, 2004), 4 pages.

Examination Report dated Sep. 11, 2009 European patent application No. 04781453.8 (filed Aug. 19, 2004), 2 pages.

Examination Report dated Aug. 3, 2010 European patent application No. 04781453.8 (filed Aug. 19, 2004), 4 pages.

Examination Report mailed Feb. 25, 2009 for Japanese patent application No. 2006-523995 (filed Aug. 19, 2004), 7 pages.

Examination Report mailed Feb. 8, 2010 for Japanese patent application No. 2006-523995 (filed Aug. 19, 2004), 4 pages.

Written Opinion dated Nov. 14, 2005 for PCT patent application No. PCT/US04/26759 (filed Aug. 19, 2004), 5 pages.

International Preliminary Report on Patentability dated Feb. 21, 2006 for PCT patent application No. PCT/US04/26759 (filed Aug. 19, 2004), 6 pages.

\* cited by examiner

FIG. 4a
FIG. 4b
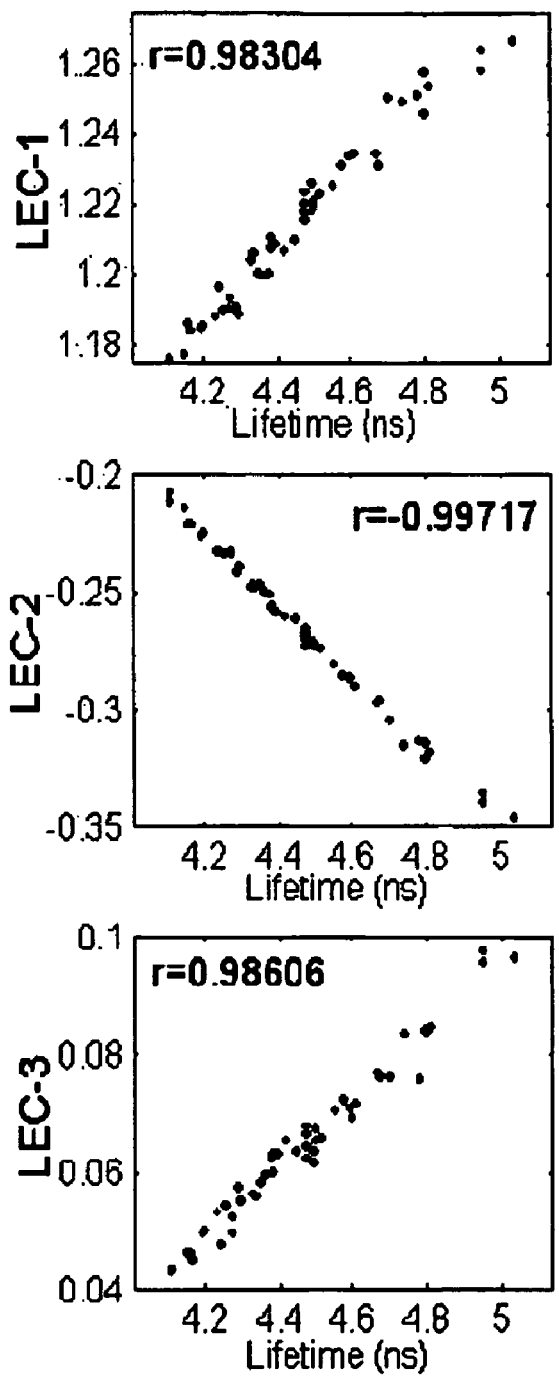
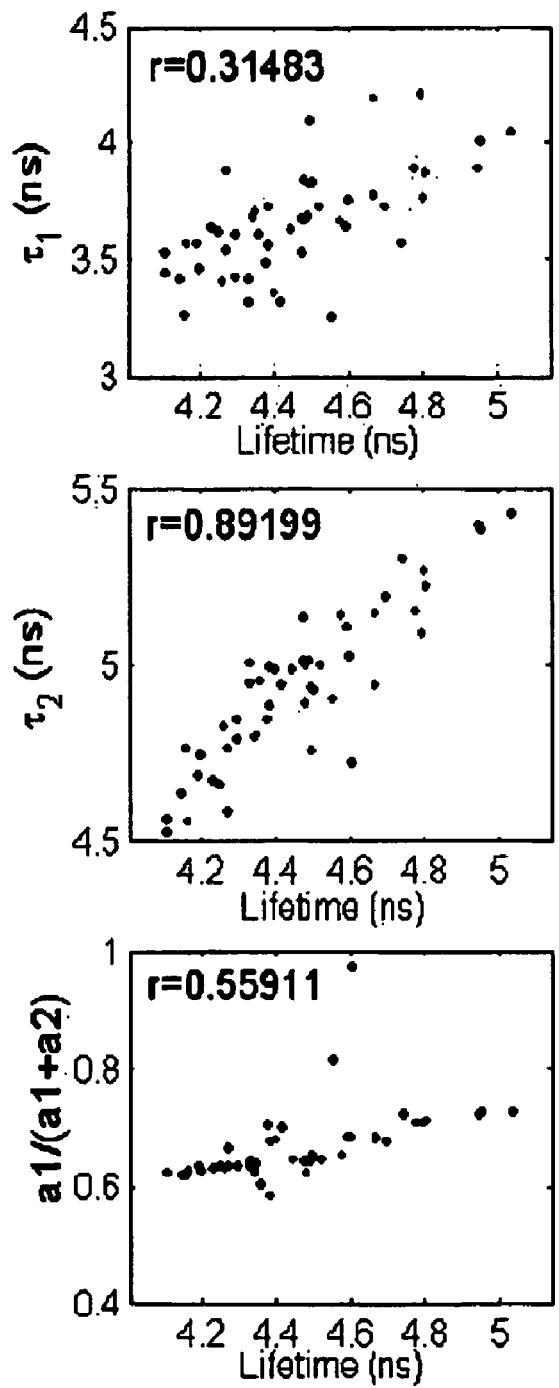

Rose Bengal in Ethanol – FLIM Lagerre Fit

METHOD FOR FLUORESCENCE LIFETIME IMAGING MICROSCOPY AND SPECTROSCOPY

This application is the National Phase of International Application PCT/US04/26759, filed Aug. 19, 2004, which designated the U.S. and that International Application was published under PCT Article 21(2) in English. This application also includes a claim of priority under 35 U.S.C. §119(e) to U.S. provisional patent application No. 60/496,316, filed Aug. 19, 2003.

GOVERNMENT RIGHTS

The U.S. Government has certain rights in this invention pursuant to Grant No. R01-HL-67377 awarded by the National Institutes of Health.

FIELD OF INVENTION

Embodiments of the present invention relate to the quantitative and qualitative analysis of time resolved fluorescence emission data and fluorescence lifetime imaging microscopy data which may be used in applications in a broad range of fields including medicine, biology, biochemistry, chemistry, pharmaceutics, genetics, and others fields requiring analysis of fluorescence emission.

BACKGROUND OF THE INVENTION

Fluorescence spectroscopy is a nondestructive optical method extensively used to probe complex biological systems, including cells and tissues for biochemical, functional and morphological changes associated with pathological conditions. Such approaches have potential for noninvasive diagnosis in vivo. Fluorescence measurements can be categorized as either static (steady-state or time-integrated) or dynamic (time-resolved). While steady-state techniques provide an integrate spectrum over time that gives information about fluorescence emission intensity and spectral distribution, time-resolved techniques measure the dynamically evolving fluorescence emission, providing additional insight into the molecular species of the sample (e.g., the number of fluorescence species and their contribution to the overall emission), and/or changes in the local environment.

Two methods for time-resolved fluorescence measurements are widely used: the time-domain and the frequency-domain. For time-domain, the sample is excited with a short pulse of light (typically nanosecond or shorter), and the emission intensity is measured following excitation with a fast photodetector. In the frequency-domain, an intensity-modulated light induces the sample fluorescence. Due to the fluorescence relaxation lifetime of the sample, the emitted wave is delayed in time relative to the excitation, inducing a phase-shift, which is used to calculate the decay time.

In the context of time-domain measurements, the fluorescence Impulse Response Function (IRF) contains all the temporal information of a single fluorescence decay measurement. The IRF is the system response to an ideal d-function excitation. In practice, the excitation light pulses are, typically, at least several picoseconds wide. Thus they should be taken as a train of d-functions with different amplitudes; each one initiating an IRF from the sample, with intensity proportional to the height of the d-function. The measured intensity decay function is the sum of all IRFs starting with different amplitudes and at different times. Mathematically, the measured fluorescence intensity decay data is given by the convolution of the IRF with the excitation light pulse. Thus, to estimate the fluorescence IRF of a compound, the excitation light pulse must be deconvolved from the measured fluorescence intensity pulse.

When the excitation light pulse is sufficiently short, resembling a d-function excitation, the measured fluorescence decay would closely resemble the intrinsic IRF. Currently, very short (femtoseconds) excitation light pulses can be generated; although for their lack of general availability, picosecond lasers are still the most widely used light sources for time-resolved measurements. Therefore, in many cases the intrinsic fluorescence IRF of the investigated compounds will have lifetimes on the order of the excitation light pulse width, and subsequently, an accurate deconvolution technique becomes crucial.

Deconvolution methods are usually divided into two groups: those requiring an assumption of the functional form of the IRF, such as the nonlinear least-square iterative reconvolution method, and those that directly give the IRF without any assumption, such as the Fourier and Laplace transform methods, the exponential series method, and the stretched exponential method, among others. In addition to these methods, an alternative approach known as global analysis, in which simultaneous analysis of multiple fluorescence decay experiments are performed, has proven useful for both time- and frequency-domain data. Among these methods, however, the most commonly used deconvolution technique is the nonlinear least-square iterative reconvolution (LSIR) method. This technique applies a least-squares minimization algorithm to compute the coefficients of a multi-exponential expansion of the fluorescence decay. In complex biological systems, fluorescence emission typically originates from several endogenous fluorophores and is affected by light absorption and scattering. From such a complex medium, however, it is not entirely adequate to analyze the time-resolved fluorescence decay transient in terms of a multi-exponential decay, since the parameters of a multi-exponential fit of the fluorescence IRF cannot readily be interpreted in terms of fluorophore content. Moreover, different multi-exponential expressions can reproduce experimental fluorescence decay data equally well, suggesting that for complex fluorescence systems there is an advantage in avoiding any a priori assumption about the functional form of the IRF decay physics.

Similarly, in the context of fluorescence lifetime imaging microscopy (FLIM), the deconvolution method is critical to data analysis. FLIM has become increasingly popular due to its ability to distinguish fluorophores differing in lifetime but with similar spectral features. Most current methods of FLIM analysis require the assumption that the excitation pulses are negligibly short, so that the fluorescence emission can be approximated to the intrinsic fluorescence decay or IRF and that the IRF follows a monoexponential decay law. However, the required assumptions of a short excitation pulse and of a single exponential fluorescence decay cannot often be fulfilled in practice, where most laser excitation pulses are several picoseconds wide and multiple fluorophores in the same specimen are simultaneously excited. Under these conditions, a deconvolution algorithm needs to be applied and a more general fluorescence decay law needs to be assumed.

Further, because fluorescence lifetimes in imaging are determined on a pixel-by-pixel basis, iterative methods for recovering the time decays can be time consuming and generally require the acquisition of a considerable number of data samples.

Expansion on the discrete time Laguerre basis as a way of deconvolving the intrinsic properties of a dynamic system from experimental input-output data was initially proposed by Marmarelis, and applied to linear and nonlinear modeling of different physiological systems including renal auto-regulation and autonomic control of heart rate. A Laguerre based deconvolution technique was recently reported as a variant of the LSIR technique, in which the fluorescence IRF is expressed as an expansion on the discrete time Laguerre basis instead of a weighted sum of exponential functions. The Laguerre deconvolution technique has been previously applied to optical spectroscopy of tissues with promising results to the analysis of time-resolved fluorescence emission data from atherosclerotic lesions, and temporal spread functions of transmitted ultrafast laser pulses through different types of human breast tissue. Further, in Marcu et al., U.S. Pat. No. 6,272,376, which is incorporated by reference herein in its entirety as if fully set forth, the Laguerre deconvolution technique was applied to time-resolved, laser-induced fluorescence spectroscopy (TR-LIFS) and used to characterize tissue by investigating the fluorescence response of protein and lipid fluorophore components in both spectral and time domains. However, a formal evaluation of this technique, as it applies to fluorescence measurements, has not been reported.

Accordingly, a need exists for methods and systems for the quantitative and qualitative analysis of time resolved fluorescence emission data and fluorescence lifetime imaging microscopy data which are both accurate and quick.

SUMMARY OF THE INVENTION

The present invention discloses a method and system utilizing conventional tools for generation and measurement of fluorescence for the analysis of fluorescence emission decay data which describes the intensity and the lifetime (temporal) characteristics of the fluorescence emission of a biochemical system in terms of a set of quantitative descriptors. The descriptors correspond to the coefficients of an expansion of the intrinsic fluorescence emission decay on an orthogonal family of mathematical functions, known as the Laguerre basis. The intrinsic fluorescence decay h(n) of a chemical/biochemical sample is thus expressed as:

$$h(n) = \sum_{j=0}^{L-1} c_j b_j^\alpha(n)$$

where $c_j$ are the expansion coefficients and represent the descriptors used by this method. These descriptors completely characterize the time-resolved and steady-state fluorescence spectra of the sample. These descriptors can be directly used to calibrate fluorescence time-resolved data for the prediction of concentrations in a mixture of chemical/biochemical components, allowing for direct characterization and classification of biochemical systems.

The present invention provides several advantages over the prior techniques including the multi exponential LSIR method. By way of example, the expansion of an intrinsic fluorescence intensity decay of any form on the Laguerre function basis can always be found, without assuming any functional form of the decay law, and more importantly, the set of expansion coefficients is unique. In contrast, a multiexponential expansion may yield more than one solution even when the number of exponential or the values of the decay constants are prefixed. Additionally, the Laguerre technique performs faster than the multiexponential LSIR, which is of a significant importance in the context of fluorescence lifetime imaging, where deconvolution must be applied for every pixel of the image. Further, the Laguerre expansion coefficients are highly correlated with the intrinsic lifetime values, suggesting that the use of these coefficients represents a new approach to characterize biochemical compounds in terms of their fluorescence lifetime properties. For the multiexponential method, although the estimated average lifetime is always correlated with the intrinsic intensity decay lifetime, the individual multiexponential parameters (decay constants and pre-exponential coefficients) may not necessarily be correlated to the intrinsic lifetimes.

In addition, other embodiments of the present invention are directed to a robust and extremely fast method for the quantitative analysis of FLIM data. This method uses the Laguerre deconvolution technique to estimate the IRF at every pixel of the data and generate lifetime maps for a sample. The excitation pulse is deconvolved from the measured images. A first expansion coefficient is estimated using the images. A coefficient map for the first expansion coefficient is generated. After removal from the images of the time-resolved information coming from the first expansion coefficient, the next higher expansion coefficient map may be estimated using a similar approach. Once the maps of all the expansion coefficients are estimated, the map of lifetimes can be computed by constructing IRF at every pixel, for S number of time instances:

$$h(r, n) = \sum_{j=0}^{L-1} c_j(r) \cdot b_j^\alpha(n), \ n = 0, 1, \ldots, S-1$$

Finally, the lifetimes map is computed by interpolating the time point at which the IRF becomes 1/e of its maximum value.

This method provides several advantages over current algorithms for time resolved fluorescence imaging. By way of example, the intrinsic fluorescence intensity decays of any form can be estimated at every pixel as an expansion on a Laguerre basis, without a priori assumption of their functional form. Additionally, the number of images required to expand the fluorescence IRF from each pixel is significantly low, thus allowing the reduction of the acquisition time. In one embodiment, the number of images required may be as few as five. However, the number of required images need not be limited to five and in alternate embodiments the number of images required may be greater than or less than five. This is of special relevance in the context of functional fluorescence lifetime imaging, where real-time acquisition is required. Still further, because deconvolution of the excitation light pulse from the measured images is actually performed at every pixel, excitation with ultra-short pulse is no longer required.

Therefore, this method has the potential to allow development of less expensive and complex FLIM systems that could be used in a variety of practical applications. By way of example, the inventive analytical method takes advantage of the orthogonality of the Laguerre functions and allows computing the complete maps of expansion coefficients extremely quickly. Because the set of expansion coefficients summarize temporal properties of the IRF that they expand, a complete characterization of the fluorescence decay at every pixel of the image can be achieved in a few seconds.

Furthermore, the maps of expansion coefficients can also be directly used to predict maps of concentrations in a mixture of chemical/biochemical components, allowing not only for the estimation of the spatial distribution of biochemical components on the sample area, but also of their relative concentration.

In light of the advantages noted above, the embodiments of the present invention may be utilized in a variety of fields including biological and biomedical research, clinical diagnosis, chemical, biochemical and pharmaceutical research, genetic research, and many others. As such, the present invention may used in a wide variety of applications including, but not limited to, the estimation of relative concentration from a mixture of biochemical components, the intra-operative identification of tumor versus normal brain (e.g., during neurosurgical resection of brain tumors), the characterization of the biochemical composition of atherosclerotic plaques, and the identification of predictor marks of plaque rupture.

Embodiments of the present invention may be implemented in a variety of ways, including computer software, which may be executed on a personal computer or server. In addition, the embodiments of the present invention may be used in conjunction with any analytical instrument that uses lifetime fluorescence spectroscopy as a sample detection/analysis technique, including, but not limited to, spectrophotometers, cytometers, and drug discovery analysis systems. Alternate embodiments of the invention may be used in conjunction with FLIM microscopy systems and spectroscopic instrumentation using fluorescence time-resolved emission data. Still further embodiments of the present invention may incorporate the inventive methods in alternate equipment, instrumentation and laboratory devices, as will be readily appreciated by those of skill in the art and implemented by routine practices.

BRIEF DESCRIPTION OF THE FIGURES

FIGS. 4a and 4b illustrate graphs of correlation between the actual lifetime values of the simulated data with the Laguerre expansion coefficients (LEC-1 to LEC-3) and the multiexponential LSIR parameters, in accordance with an embodiment of the present invention.

DETAILED DESCRIPTION

Figure 1:
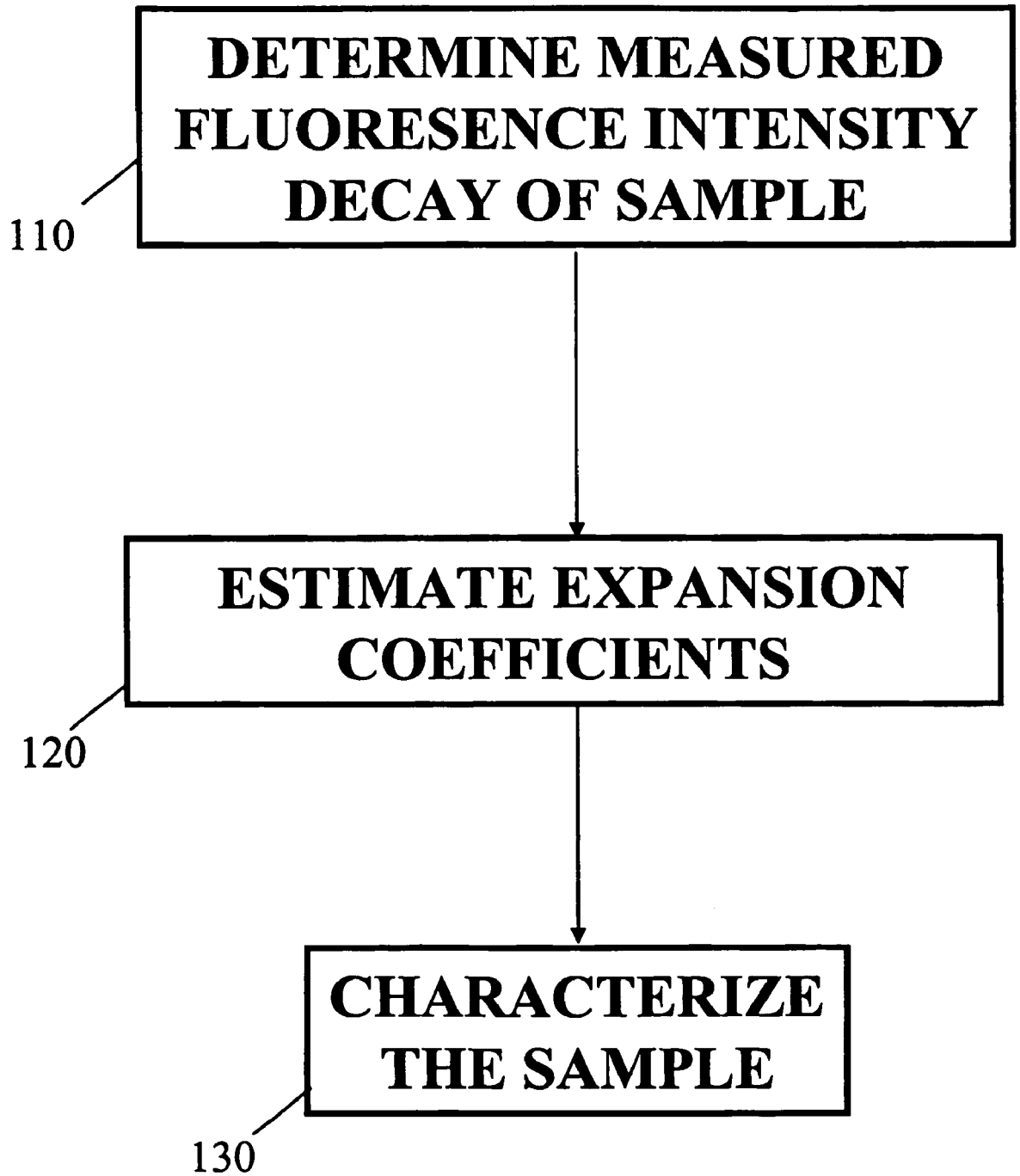
FIG. 1 illustrates a block diagram of a method for obtaining fluorescence measurements according to an embodiment of the present invention.

FIG. 1 illustrates a block diagram of a method for obtaining a fluorescence measurement of a sample according to an embodiment of the present invention. The sample may be excited with a short pulse of light. In Block 110 determine the measured intensity decay function of a sample. The Laguerre deconvolution technique is used to estimate the intrinsic fluorescence intensity decay of a sample. The sample may be a biological tissue, a chemical, a biochemical sample or any combination thereof, as well as any other type of sample known in the art. It should be understood that the term tissue broadly refers to any living organism that is comprised of a collection of similar cells to perform a particular function. For example the tissue may be a portion of an arterial wall, a tumorous mass or blood plasma.

The Laguerre deconvolution technique is a nonparametric method which expands the fluorescence IRF on the discrete time Laguerre basis. The Laguerre functions (LF) have been suggested as an appropriate orthonormal basis owing to their built-in exponential term that makes them suitable for physical systems with asymptotically exponential relaxation dynamics. Because the Laguerre basis is a complete orthonormal set of functions, a unique characteristic of this approach is that it can reconstruct a fluorescence response of arbitrary form. Thus, the Laguerre basis represents a unique and complete expansion of the decay function. The measured fluorescence intensity decay data y(t) is given by the convolution of the IRF h(t) with the excitation light pulse x(t):

$$y(t) = \int_0^t h(\tau)x(t-\tau)d\tau \tag{1}$$

The time-domain time-resolved fluorescence measurements, however, are often obtained in discrete time, as in the case of pulse sampling and gated detection technique (direct recording of fluorescence pulse with a fast digitizer). In a discrete-time case the relationship between the observed fluorescence intensity decay pulse and the excitation laser pulse is expressed by the convolution equation:

$$y(n) = T \cdot \sum_{m=0}^{K-1} h(m)x(n-m), n = 0, \ldots, K-1 \tag{2}$$

The parameter K in equation (2) determines the extent of the system memory, T is the sampling interval, and h(m) is the intrinsic fluorescence IRF. The Laguerre deconvolution technique uses the orthonormal set of discrete time LF $b_j^\alpha(n)$ to discretize and expand the fluorescence IRF:

$$h(n) = \sum_{j=0}^{L-1} c_j b_j^\alpha(n) \tag{3}$$

In equation (3), $c_j$ are the unknown Laguerre expansion coefficients (LEC). As indicated in Block 120, the expansion coefficients are estimated. These expansion coefficients may be estimated based on input-output data; $b_j^\alpha(n)$ denotes the $j^{th}$ order orthonormal discrete time LF; L is the number of LF used to model the IRF. The LF basis is defined as:

$$b_j^\alpha(n) = \alpha^{(n-j)/2}(1-\alpha)^{1/2} \sum_{k=0}^{j} (-1)^k \binom{n}{k}\binom{j}{k} \alpha^{j-k}(1-\alpha)^k, \tag{4}$$

$$n \geq 0$$

The order j of each LF is equal to its number of zero-crossing (roots). The Laguerre parameter ($0<\alpha<1$) determines the rate of exponential decline of the LF. The higher the order j and/or the larger the Laguerre parameter $\alpha$, the longer the spread over time of a LF and the larger the time separation between zero-crossing. It is important to note that the Laguerre parameter $\alpha$ defines the time scale for which the Laguerre expansion of the system impulse response is most efficient in terms of convergence. Thus, fluorescence IRF with longer lifetime (longer memory) may require a larger $\alpha$ for efficient representation. Commonly, the parameter $\alpha$ is selected based on the kernel memory length K and the number of Laguerre functions L used for the expansion, so that all the functions decline sufficiently close to zero by the end of the impulse response.

By inserting equation (3) into equation (2), the convolution equation (2) becomes:

$$y(n) = \sum_{j=0}^{L-1} c_j v_j(n) \tag{5}$$

$$v_j(n) = T \sum_{m=0}^{K-1} b_j^\alpha(m) x(n-m)$$

where $v_j(n)$ are the discrete time convolutions of the excitation input with the LF and denoted as the "key variables". The computation of the $v_j(n)$ can be accelerated significantly by use of the recursive relation:

$$v_j(n) = \sqrt{\alpha} v_j(n-1) + \sqrt{\alpha} v_{j-1}(n) - v_{j-1}(n-1) \tag{6}$$

which is due to the particular form of the discrete-time LF. Computation of this recursive relation must be initialized by the following recursive equation that yields $v_0(n)$ for a given stimulus x(n):

$$v_0(n) = \sqrt{\alpha} v_0(n-1) + T\sqrt{\sqrt{1-\alpha}} x(n) \tag{7}$$

These computations can be performed fast, for n=0, 1, . . . , N and j=0, 1, . . . , L−1; where N is the number of samples in the data sets and L is the total number of LF used in the IRF expansion. Finally, the unknown expansion coefficients can be estimated by generalized linear least-square fitting of equation (5) using the discrete signals y(n) and $v_j(n)$. The optimal number of LF to be used in the model and subsequently, the value of the parameter $\alpha$ was determined by minimizing the weighted sum of the residuals:

$$S = \sum_{n=0}^{N-1} w_n [y(n) - \hat{y}(n)]^2 \tag{8}$$

where y(n) is the real fluorescence decay, $\hat{y}(n)$ is the estimated decay, and $w_n$ is the weighting factor. The weight $w_n$ is proportional to the inverse of the experimental variance $\sigma_n^2$ for the measurements at time n. For time-correlated single photon-counting, which is the most common technique for time-domain measurements, it is straightforward to compute the experimental variance, since this is assumed to follow Poisson statistics, where the variance is known to be proportional to the number of photon counts. Direct recording of the fluorescence pulse with a fast digitizer may also be used to make time-domain measurements. In this case, however, the experimental variance needs to be estimated from a representative set of experimental data. To estimate the experimental variance as a function of the amplitude of the fluorescence decay, repeated measurements of the sample fluorescence decay are taken, and the variance and the average intensity at each time point n of the decay signals are then computed. The slope of the straight-line fit through a log-log plot of the variance as a function of the average intensity would indicate the relation between the experimental variance and the fluorescence intensity decay amplitude.

For time-correlated single photon-counting, the experimental variance was estimated from 55 repeated fluorescence decay measurements of 6 different fluorescence standard dyes at their peak wavelengths. The variance was represented in log-log scale as a function of the average of the 55 measurements, and the average slope of the straight-line fits through the log-log plots for the 6 data sets was 0.99 (range: 0.91-1.09), suggesting that the experimental variance increased almost proportionally with the fluorescence signal. Thus, weight $w_n$ was estimated by 1/y(n).

Finally, the Laguerre expansion coefficients may be used to characterize samples 130 in terms of their fluorescence temporal properties.

Figure 2:
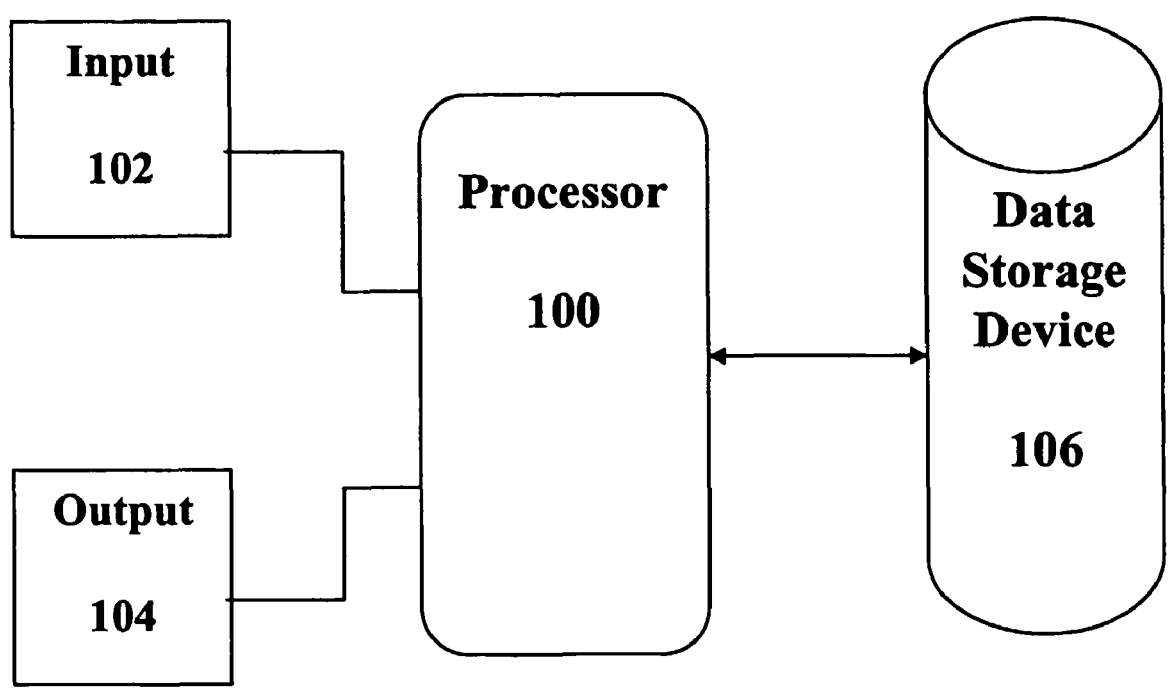
FIG. 2 illustrates a block diagram of a system for implementing a method of an embodiment of the present invention.

FIG. 2 illustrates a system employing a method according to an embodiment of the present invention. The measured fluorescence intensity decay may be received by processor 100 via Input 102. Input 102 may be coupled to a fluorescence microscope which may be used to determine the measured fluorescence intensity decay. Alternatively, the measured fluorescence intensity decay may be input manually at input 102, which may be a computer terminal or a keyboard. In alternate embodiments of the present invention, input 102 may be selected from any electronic or similar instrument that can generate, collect or otherwise provide the type of data that may be processed in accordance with the inventive methods, as will be readily appreciated by those of skill in the art, and which can be implemented by routine experimentation. Further, input 102 may include or be coupled to an excitation light source (not shown) to generate an excitation pulse. The excitation light source may be any such source as is known in the art including, but not limited to, a nitrogen laser or an ultraviolet laser. Processor 100 may then be used to deconvolve the excitation pulse from the measured fluorescence intensity decay to estimate the intrinsic fluorescence intensity decay using the Laguerre deconvolution method. The processor 100 may estimate the Laguerre expansion coefficients which may be output via output 104 or stored in storage device 106 for further use evaluating the accuracy or speed of the technique or in characterizing a sample.

The performances of the Laguerre deconvolution technique and proposed method for the prediction of concentrations in a mixture of biochemical components based on the Laguerre expansion coefficients were assessed with simulated and experimental data. The radiative lifetime value, $\tau_f$, a given IRF was calculated by interpolating the time point at which the IRF becomes 1/e of its maximum value. A brief description of the simulated data generation and of the fluorescence measurements on lifetime fluorescence standards is presented in the next section.

Generation of Time-Resolved Fluorescence Data

Simulated Data

The synthetic data was generated by means of a four-exponential model, with fixed decay constants and random values for the fractional contribution of each exponential component. A total of 600 data sets were generated, yielding average lifetime values between 0.3-12 ns. White noise of zero mean and three different variance levels was added to the data, yielding three different groups of 600 data sets, with approximately 80 dB, 60 dB and 50 dB signal-to-noise ratios (low-noise, medium-noise and high-noise level groups, respectively). A laser pulse (700 psec pulse width) measured from a sample of 9-cyanoanthracene was used as the excitation signal for our simulation. Therefore, all the data sets were convolved with the laser signal, yielding the "measured" decay data for our simulation. The Laguerre deconvolution technique was applied to this data, using different model orders ranging from 3-6 Laguerre functions. Similarly, the multi-exponential deconvolution technique was also applied to the data, using different model orders ranging from 1-4 exponential components.

Experimental Data: Lifetime Fluorescence Standards

Data was collected from standard dyes for fluorescence lifetime measurements. The dyes were selected to cover a broad range of radiative lifetimes (0.54 to 12 ns) that are most relevant for biological applications such as fluorescence emission from tissue. The fluorophores chosen included Rose Bengal (33,000, Sigma-Aldrich), Rhodamin B (25,242, Sigma-Aldrich), and 9-cyanoanthracene (15,276, Sigma-Aldrich). The fluorescence dyes used in the measurements were diluted into 10-6 M solutions. The fluorescence standard samples were excited with a sub-nanosecond pulsed nitrogen laser with emission wavelength 337.1 nm (700 spec WHOM). The fluorescence response was measured using a time-resolved time-domain fluorescence apparatus allowing for direct recording of the fluorescent pulse (fast digitizer and gated detection). Fluorescence pulse was collected by a fiber optic bundle (bifurcated probe) and directed to a monochromator connected to a multi-channel plate photo-multiplier tube with a rise time of 180 ps. The entire fluorescence pulse from a single excitation pulse was recorded with a 1 GHz bandwidth digital oscilloscope. For each sample solution, the time-resolved fluorescence spectra were measured for a 200 nm spectral range from 400 nm to 650 nm at 5 nm increments. After each measurement sequence, the laser pulse temporal profile was measured at wavelength slightly below the excitation laser line. Background spectra were taken for the solvents (ethanol or methanol) using the same cuvette.

Technique Evaluation and Validation

Simulated Data

Figure 3A:
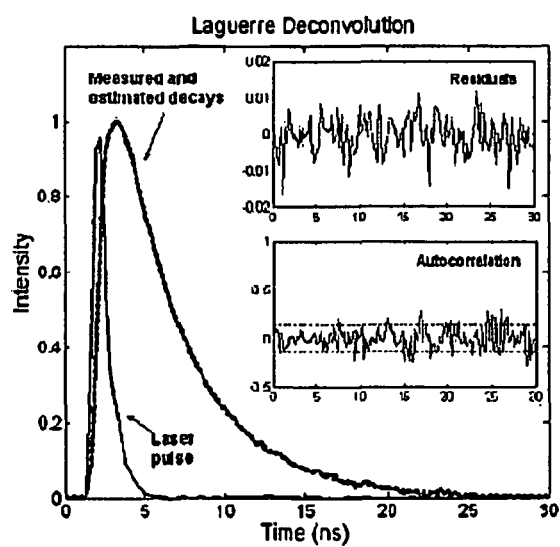
FIGS. 3a and 3b illustrate sample simulated fluorescence decay trace (solid gray, t=4.1 ns) and its corresponding estimated decay traces (dotted black) with the Laguerre and multiexponential methods, together with the laser pulse (solid black), in accordance with an embodiment of the present invention.
Figure 3B:
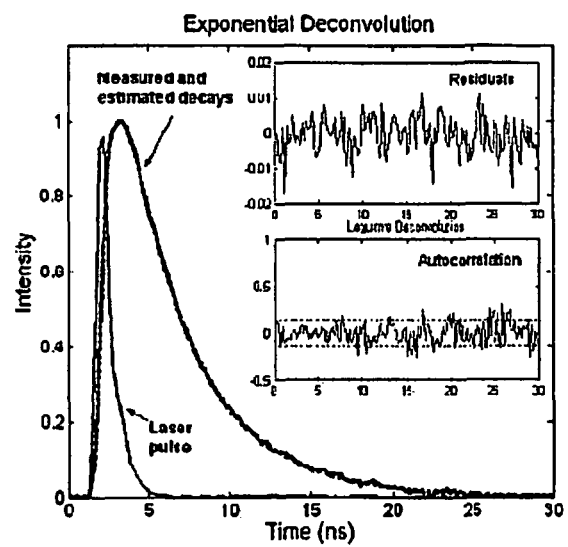

FIG. 3a illustrates a graph of the simulated time-resolved fluorescence intensity decay (solid gray, $\tau=4.1$ ns at medium-noise level), its corresponding estimation by the Laguerre deconvolution method (dotted black, L=5), and the laser pulse (solid black). The residuals (top inset) are <2% of the peak fluorescence amplitude and they appear randomly distributed around zero. The autocorrelation function of the residuals (bottom inset) does not contain low-frequency oscillations characteristic of nonrandom residuals, and is mostly contained within the 95% confidence interval (dotted lines) centered around zero. These observations indicate an excellent fit between the synthetic and estimated fluorescence decays, showing that the fluorescence IRF was properly estimated with the deconvolution algorithm based on the Laguerre expansion technique. The results for the same sample fluorescence decay using the multi-exponential approach (P=3), presented in FIG. 3b, showed similar results. One important detail depicted in FIG. 3a and FIG. 3b is that the residuals and autocorrelation functions corresponding to both the Laguerre and multi-exponential fits look very much alike. This is explained by the fact that both techniques were able to accurately fit the true synthetic time-resolved decay data, leaving out just the additive white noise component of the artificial data.

The performance of Laguerre and multi-exponential deconvolution techniques along the lifetime range of 0.3-12 ns was assessed by means of the relative error between the real and the estimated lifetime values (RLE), and the normalized mean square error (NMSE). Similar performances were obtained for both techniques: the RLE values were found below 1%, 2% and 4%, whereas the NMSE values were smaller then 0.04%, 0.3% and 0.9% for the low-, medium- and high-noise level groups, respectively.

To investigate the effect of the number of LF (chosen to expand the fluorescence IRF) on the estimation of the intrinsic fluorescence decay, the synthetic data was deconvolved using Laguerre expansions of different orders (3 to 6 LF). For decays with lifetimes ranging from 1 to 8 ns, the IRF expansion with 5 LF yielded the best estimation of the fluorescence emission decay (RLE<2%). The best estimate for fast decays ($\tau_f<1$ ns) and for slow decays ($\tau_f>8$ ns) were obtained using an expansion of 6 LF and 3-4 LF, respectively. For the multi-exponential deconvolution method, a good estimation of the IRF (RLE<2%) was yielded by bi-exponential expansion for slow decays and tri-exponential expansion for fast decays.

As stated above, it is important that a deconvolution technique provides a representation of the intrinsic temporal fluorescence dynamics to be used for further characterization of the investigated compound. Both the multi-exponential and Laguerre deconvolution techniques summarize the temporal fluorescence intensity decay information in terms of the parameters of the model they use to represent the fluorescence IRF: i) the pre-exponential factors ($\alpha_i$) and the decay constants ($\tau_i$) for the case of the multi-exponential approach, and ii) the Laguerre $\alpha$ parameter and the $c_j$ expansion coefficients for the case of Laguerre approach. Therefore, a natural attempt to characterize a compound in terms of its fluorescence lifetime information is to utilize either the multiexponential or the Laguerre model parameters.

To investigate whether these model parameters reflect by themselves the fluorescence temporal information of the investigated compound, the correlation coefficients between the actual lifetime values of the simulated data and the model parameters (first two exponential parameters and first three Laguerre expansion coefficients) were computed. For a bivariate case, the correlation coefficient ($-1<r<1$) is defined as the covariance between the two variables normalized by the variances of each variable, and measures the strength of the linear relationship between the two variables. A correlation coefficient $r=-1$ indicates a perfect negative (inverse) linear dependence, $r=0$ indicates no linear dependence, and $r=1$ indicates a perfect positive linear dependence.

The first three Laguerre expansion coefficients as a function of the radiative lifetime between 4-5 ns and the correlation coefficients are shown in FIG. 4a. It can be clearly observed the 1st and 3rd expansion coefficients were positively correlated with the intrinsic decay lifetime, whereas the 2nd expansion coefficient was negatively correlated with the intrinsic lifetimes. All three Laguerre expansion coefficients (LEC-1 to LEC-3) were highly correlated to the real lifetime values ($r>0.95$). This result indicates that each of the Laguerre expansion coefficients capture and reflect the temporal relaxation of the IRF, and thus can be further used for the characterization of the investigated compound.

Plots of the bi-exponential fast ($t_1$) and slow ($t_2$) decay constants and of the relative contribution of the fast exponential ($a_1/(a_1+a_2)$) as a function of the radiative lifetime between 4-5 ns are also shown in FIG. 4b. For this particular lifetime range, only one of the time-decay constants, the slow decay constant ($t_2$), was positively correlated ($r=0.82\pm0.01$) with the lifetime values. The remaining time decay constant and the normalized pre-exponential factors were not correlated with the lifetime values ($r=0.55\pm0.02$ and $r=0.54\pm0.03$, respectively).

Experimental Data

Figure 5A:
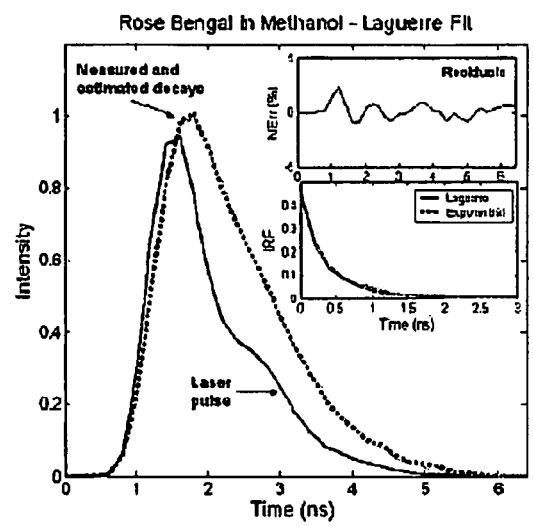
FIGS. 5a and 5b illustrate graphs of the measured time-resolved decays from Rose Bengal in methanol at 580 nm together with the laser traces and the corresponding fits by the Laguerre and the exponential approaches, in accordance with an embodiment of the present invention.
Figure 5B:
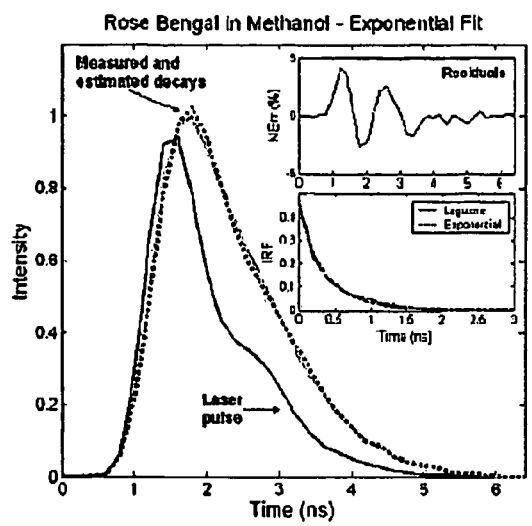

To investigate the accuracy of Laguerre deconvolution method of retrieving fluorescence decays from experimental data, a number of lifetime fluorescence standards with a broad range of relaxation lifetimes were measured in solutions. The lifetimes retrieved by both the Laguerre and the multi-exponential deconvolution methods were compared with values from the literature (see Lakowicz, "Principles of Fluorescence Spectroscopy, $2^{nd}$ ed." *Kluwer Academic/Plenum*, New York (1999)). The results of this analysis are presented in Table 1 (mean±SE).

models of L=3 or L=4 or a single-exponential decay. As shown in FIGS. 5a and 5b, both methods yielded very good fits, although for this particular example, the Laguerre approach performed better, as indicated by the smaller Laguerre residuals (top insets of FIG. 5a). Both the Laguerre and the exponential methods yielded similar intrinsic fluorescence decays (IRF) with lifetime values of 0.456±0.004 ns and 0.4±0.006 ns, respectively, which were in good agreement with previously reported data.

Figure 6A:
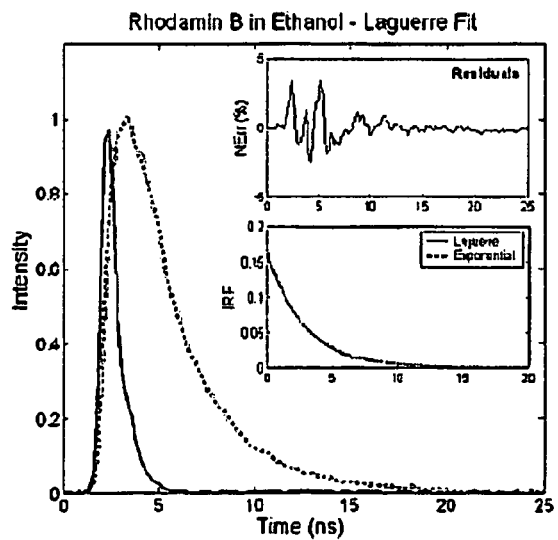
FIGS. 6a and 6b illustrate graphs of the measured time-resolved decay from Rhodamin B in ethanol at 590 nm with the laser traces and the corresponding fits by the Laguerre and the exponential approaches, in accordance with an embodiment of the present invention.
Figure 6B:
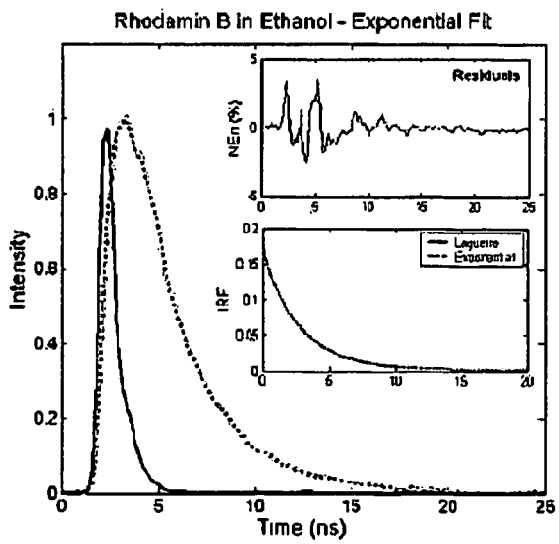

Similarly, measurements of Rhodamin B in ethanol and methanol demonstrated the ability of the Laguerre method to accurately resolve nanosecond and sub-nanosecond fluorescence lifetimes (FIG. 6a), which is of special importance because a number of biologically relevant fluorophores (e.g., elastin, collagen) are known to emit at these time scales. The RdmB fluorophore intensity decay data was best fitted to Laguerre models of L=4 and to a single exponential decay. Both methods yielded very good fits as can be seen in FIG. 6a and FIG. 6b.

Figure 7A:
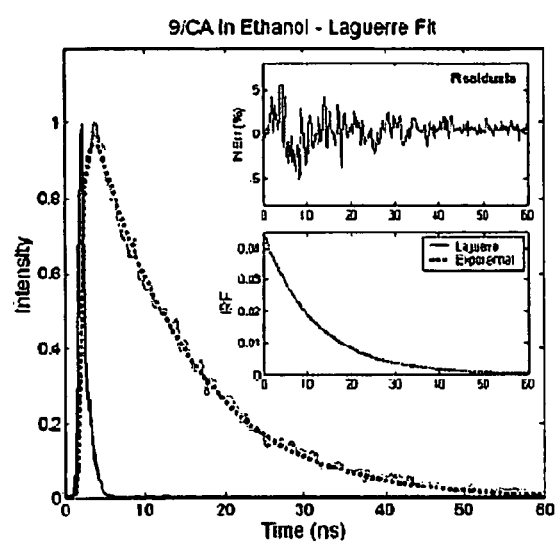
FIGS. 7a and 7b illustrate graphs of the measured time-resolved decays from 9/CA in ethanol at 445 nm, shown with the laser traces and the corresponding fits by the Laguerre and the exponential approaches, in accordance with an embodiment of the present invention.
Figure 7B:
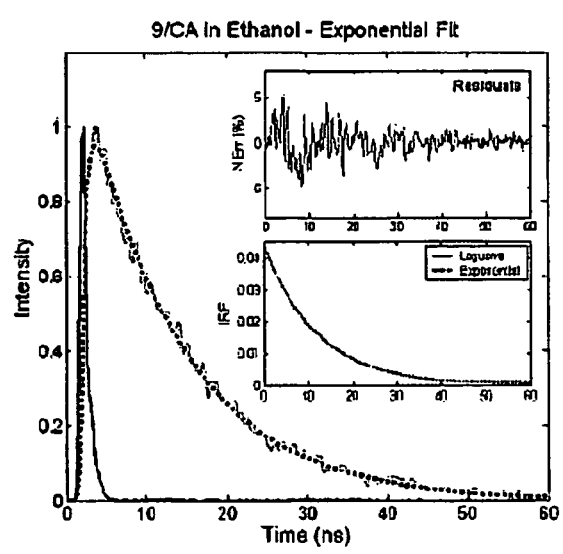

Finally, to assess the ability of the Laguerre technique to retrieve long fluorescence lifetimes, the fluorescence decay of 9-cyanoanthracene (9/CA) in ethanol was also deconvolved (FIG. 7a and FIG. 7b). Both the Laguerre and the exponential methods yielded similar intrinsic fluorescence decays with lifetime values (see Table 1 above) also in agreement with previous reports. The 9/CA fluorophore intensity decay data was best fitted to Laguerre models of L=2 and to a single exponential decay, and very good fits were attained by the two methods as observed in FIG. 7a and FIG. 7b. Similar to the results on the simulation data, it was observed that deconvolution of long-lived fluorophores (e.g., 9/CA) require fewer LF for expansions when compared with the short-lived compounds (e.g., RB and RdmB).

To compare the computational time of both the Laguerre and the multiexponential deconvolution techniques, 250 sets of 9/CA time-resolved fluorescence data at several wavelengths (400-650 nm) were deconvolved using both techniques, and the deconvolution time was measured for each set of data. The average computational time was 33.1±0.86 ms for the Laguerre deconvolution with 5 LF, and 101.4±1.6 ms for the LSIR deconvolution with a single-exponential. Both methods were implemented in Matlab-6.5 and executed on an IBM-compatible workstation (Intel Xeon processor, 2.0 GHz).

TABLE 1

Lifetime values (mean ± SE) of fluorescence standard dyes estimated by the Laguerre and exponential deconvolution techniques.

| Sample | Solvent | Lifetime (ns) Laguerre | Lifetime (ns) Exponential | Literature | Wavelength (nm) |
|---|---|---|---|---|---|
| Rose Bengal | Ethanol | 0.769 ± 0.005 | 0.702 ± 0.004 | 0.850 | 590 |
| Rose Bengal | Methanol | 0.457 ± 0.004 | 0.400 ± 0.006 | 0.540 | 580 |
| Rhodamin B | Ethanol | 2.872 ± 0.015 | 2.880 ± 0.006 | 2.850 | 590 |
| Rhodamin B | DI Water | 1.533 ± 0.057 | 1.531 ± 0.024 | 1.520 | 580 |
| 9/CA | Ethanol | 11.746 ± 0.026 | 11.630 ± 0.020 | 11.850 | 445 |

Short-lived fluorophores, like Rose Bengal, with lifetimes ranging in the hundreds of picoseconds could be reliably retrieved by the Laguerre deconvolution technique. This is shown in FIG. 5a for a fluorescence intensity decay measurement from Rose Bengal in methanol at 580 nm. The fluorophore intensity decay data was best fitted to either Laguerre Applications Prediction of Concentration in Mixtures with the Laguerre Expansion Coefficients As noted above, because the Laguerre expansion coefficients contain inherent information about the fluorescence amplitude (intensity) and the temporal decay characteristics, these coefficients can be directly used for quantitative analysis of the biochemical systems. To address this, a method for the prediction of concentrations in a mixture of biochemical components based on the analysis of the Laguerre expansion coefficients of the fluorescence IRF is introduced in this section and described as follows.

The sample fluorescence IRF, S(n), can be expanded on N Laguerre functions $b_j^\alpha(n)$:

$$S(n) = \sum_{j=0}^{N-1} c_j b_j^\alpha(n) \quad (9)$$

In equation (9), $c_j$ are the expansion coefficients of the sample decay model. It is also assumed that the sample is composed of M biochemical components, each of them producing fluorescence IRF $C_k(n)$ that can also be expanded on the same N Laguerre functions:

$$C_k(n) = \sum_{j=0}^{N-1} a_{k,j} b_j^\alpha(n), k = 1, \ldots M \quad (10)$$

In equation (10) $\alpha_{k,j}$ are the expansion coefficients of the $k^{th}$ biochemical component IRF.

Finally, we assume that the sample fluorescence IRF S(n) can also be modeled as the linear combination of their M individual biochemical component fluorescence IRF $C_k(n)$:

$$S(n) = \sum_{k=1}^{M} A_k C_k(n) \quad (11)$$

where $A_k$ are the relative contributions of the individual biochemical component fluorescence IRF to the sample fluorescence IRF. Inserting equation (10) in equation (11), it can be followed that:

$$S(n) = \sum_{k=1}^{M} A_k C_k(n) \quad (12)$$
$$= \sum_{k=1}^{M} A_k \left( \sum_{j=0}^{N-1} a_{k,j} b_j^\alpha(n) \right)$$
$$= \sum_{j=0}^{N-1} \left( \sum_{k=1}^{M} A_k a_{k,j} \right) b_j^\alpha(n)$$

Finally, from equations (9) and (12), we can relate the expansion coefficients $c_j$ of the sample IRF to the expansion coefficients $\alpha_{k,j}$ of the biochemical component IRF as follows:

$$c_j = \sum_{k=1}^{M} A_k a_{k,j}, j = 1, \ldots, N \quad (13)$$

In practice, the expansion coefficients $c_j$ and $a_{k,j}$ can be estimated from the sample fluorescence intensity decay and the individual biochemical fluorescence intensity decay measurements. Therefore, it is possible to retrieve the relative contributions $A_k$ of the individual biochemical components fluorescence IRF to the sample fluorescence IRF, by solving the system of linear equations defined in (13). It is important to notice that to solve this system, the number of equations should be greater or equal to the number of unknowns (N≧M), therefore, the number of LF (N) used to expand the decay modeling should be greater or equal to the number of the individual biochemical components (M).

The method for prediction of concentrations in a mixture of biochemical components based on the analysis of the Laguerre expansion coefficients was tested on mixtures of Rose Bengal (RB) and Rhodamin B (RdmB) of distinct relative concentrations. Three types of mixture solutions were prepared with [RdmB]/[RB] concentration values equal to 0.25/0.75 µM, 0.50/0.5 µM, and 0.75/0.25 µM, respectively. The 10-6 M Rose Bengal and Rhodamin B solutions were also measured representing [RdmB]/[RB] concentrations of 0/1.0 µM and 1.0/0 µM, respectively. Time-resolved fluorescence measurements at wavelengths between 550-600 nm (corresponding to the range of wavelengths around the spectral peak at 575 nm) were recorded from the five solutions and used for the analysis.

Validation of the Concentration Prediction with Laguerre Coefficients

To test the proposed method for the prediction of concentrations in a mixture of biochemical components, fluorescence decays of five mixtures of Rhodamin B (RdmB) and Rose Bengel (RB) were expanded using 5 LF with discrete-time Laguerre parameter $\alpha$=0.81. The relative contributions ($A_k$) of the individual biochemical component decays to the mixture fluorescence decays were predicted by solving equations (13). To compare the proposed approach with more traditional methods for concentration prediction based on spectral analysis, the relative concentration of RdmB was also determined by applying principal component regression (PCR) and partial least square (PLS) to the spectral data of the mixtures. The results of the three methods are shown in Table 2.

TABLE 2

Estimated Rhodamin B concentration from the five solutions estimated by the three methods applied.

| Method | Relative Concentration of RdmB | | |
| --- | --- | --- | --- |
| | 25% | 50% | 75% |
| PCR | 22.8 ± 1.25 | 48.79 ± 1.77 | 68.66 ± 1.57 |
| PLS | 21.98 ± 1.63 | 47.31 ± 1.99 | 67.04 ± 1.69 |
| Laguerre | 25.23 ± 0.48 | 51.16 ± 0.83 | 73.86 ± 1.66 |

All methods give a close estimation of the Rhodamin B concentration in the 3 solutions. However, the Laguerre model of intrinsic fluorescence decays yielded a better estimation of the fluorophore concentrations (error<2%), compared to the spectral methods (PCR: error<7%; PLS: error<10%).

Discussion

Although a multi-exponential deconvolution has the potential to accurately retrieve the fluorescence IRF of complex biomolecular systems, the parameters of a multi-exponential fit cannot readily be interpreted in terms of number of fluorophore content. Changes of a fluorophore environment, protein conformations or cross-links, also would result in different intensity decay for a single fluorophore; thus, it is not generally practical to consider individual decay times. Moreover, very different multi-exponential expressions can reproduce the same experimental fluorescence intensity decay data equally well as demonstrated with the simulation results presented above, in which synthetic decay data generated by a four-exponential model was accurately deconvolved by multi-exponential models of different orders from 2-4 exponential components. This and previously reported evidence support the conclusion that for complex fluorescence systems, there is an advantage in avoiding any assumption about the functional form of the fluorescence decay law. Further, this suggests that the Laguerre deconvolution technique is a suitable approach for the analysis of time-domain fluorescence data of complex systems, because this technique has the ability to expand intrinsic fluorescence intensity decays of any form, without a priori assumption of its functional form.

While the results from both simulation and lifetime fluorescence standard support the conclusion that the Laguerre method performs similarly to the multi-exponential method in terms of accuracy for retrieving the fluorescence IRF, one advantage of the Laguerre method is that for any value of the Laguerre parameter $\alpha$, the corresponding basis of LF is a complete orthonormal basis. Thus, it is certain that an expansion of the fluorescence IRF on the Laguerre function basis can always be found, and even more important, the set of expansion coefficients are unique for a defined Laguerre basis. Our results showed that 3-6 LF are sufficient to expand fluorescence decays with lifetime values ranging from 0.3-12 ns, which are times relevant for the emission of tissues endogenous fluorophores. Generally, an accurate estimation of slow decays requires fewer LF for expansion (less than 3) than the fast decays (larger than 5). In contrast, deconvolution with the multi-exponential approach may yield more than one solution, even when the number of exponential or the values of the decay constants are prefixed. The span of possible solutions of a multi-exponential expansion can be significantly reduced by fixing a priori the values of the decay constants, as it was proposed in the exponential series method proposed by Ware et al., "Deconvolution of fluorescence and phosphorescence decay curves. A least square method", *J Phys Chem* 77, 2038-2048 (1973). However, it is important to note that deconvolution with the exponential series method is successful only when the prefixed decay constants are commensurate with the investigated fluorescence decay.

Another advantage of the Laguerre deconvolution over the multi-exponential LSIR results from the different methods required for estimating the expansion parameters. The Laguerre expansion technique uses a least-square optimization procedure to determine the coefficients of the Laguerre expansion of the system dynamics. For a defined Laguerre basis (i.e., given values of the parameter $\alpha$ and the number of the Laguerre functions), the problem of finding the expansion coefficients is reduced to solving an overdetermined system of linear equations (given in equation (5)), which represents a linear least square minimization problem. The same property holds even for the estimation of nonlinear dynamics that can also be formulated in terms of linear equations using the Laguerre expansion technique. In contrast, traditional multi-exponential LSIR techniques require the estimation of intrinsic nonlinear parameters (the decay constants), which represents a nonlinear least square problem. Although a number of very robust and efficient algorithms for the solution of nonlinear least square problems are available nowadays, such as the Gauss-Newton and Levenberg-Marquardt methods, solving a linear least-square problem (Laguerre technique) is a much simpler and less computationally expensive problem than finding a nonlinear least square solution (through a multi-exponential technique). This was clearly supported by the results described above on the speed of computational analysis, showing that the Laguerre deconvolution technique convergences to a correct solution approximately 3 times faster than the mono-exponential deconvolution. The convergence speed would become more significant when a bi-exponential or higher order multi-exponential expansion is used. This specific advantage of the Laguerre method becomes even more important in the context of application of lifetime fluorescence spectroscopy to clinical research of tissue diagnosis and FLIM (discussed below), where the speed of data analysis is of crucial importance.

Analysis of correlations coefficients (r) demonstrated that each Laguerre expansion coefficient is highly correlated with the intrinsic lifetime value, suggesting that the use of these coefficients has potential, as a new approach, for the direct characterization of biochemical compounds in terms of their fluorescence emission temporal properties. For the case of the multiexponential deconvolution, although the estimated (computed) average lifetime is always correlated with the intrinsic radiative lifetime, the individual multi-exponential parameters (decay constants and pre-exponential coefficients) may not necessarily be correlated to the intrinsic lifetimes. This was shown in the simulations results, where only one of the decay constants was correlated with the lifetime. This lack of correlation between individual multi-exponential parameters and the lifetime occurs because the multi-exponential model does not represent an orthogonal expansion of the fluorescence IRF; therefore, the estimated fitting parameters are not independent from each other. This condition implies that the value of one specific parameter would be determined not only by the data to be fitted, but also by the value of the other fitting parameters; thus, reducing the correlation between the actual lifetimes and the estimated values of the multi-exponential parameters. In contrast, because the Laguerre basis provides an orthogonal expansion of the IRF, the value of each expansion coefficients depends exclusively on the data to be fitted, making them highly correlated to the actual lifetime values.

This study also demonstrated that the Laguerre expansion coefficients have potential for quantitative interpretation of fluorescence decay. A new method for the prediction of concentrations in a mixture was introduced here and successfully tested on fluorescence standards components (Rhodamin B and Rose Bengel). Moreover, using only fluorescence decay information from a narrow spectral range, this method yielded improved prediction of the fluorophore concentrations when compared to that obtained using traditional methods of spectral analysis (PCR and PLS). While not wishing to be bound by any particular theory, one possible explanation for this result is that spectral methods use only the information derived from spectral distribution of fluorescence intensity, while the proposed Laguerre method uses both the amplitude and temporal information of the fluorescence emission from a predefined narrow spectral range. Emission spectra of RdmB and RB are highly overlapped, thus spectral emission alone would provide limited information for the prediction of their relative concentration. However, RdmB and RB present different fluorescence decay characteristics, which were taken into account together with the amplitude information when the Laguerre coefficients are used for concentration prediction. Although in this study the proposed Laguerre method uses only the amplitude and temporal information of the fluorescence emission from a predefined narrow spectral range, the Laguerre expansion coefficients corresponding to fluorescence IRF taken at multiple emission wavelengths reflect also the spectral information of the fluorescence emission. This spectral information could be also integrated into a more advanced method for characterization and discrimination of a biological system.

It is also noteworthy that an analogous method for the prediction of concentrations in a mixture of biochemical components based on the multi-exponential model of intrinsic fluorescence decay could also be implemented. Because such a method would also use both the amplitude and temporal information contained by fluorescence data, it would most likely yield similar performance to that of the Laguerre method presented herein. However, a method based on the multi-exponential expansion would require that the decay constants would be chosen a priori. Therefore, one disadvantage of the approach based on the multi-exponential model would represent the need for a "good guess" of the decay constants (these must be commensurate with the investigated fluorescence decays), in order to ensure an acceptable prediction of the investigated concentrations. A further requirement for such technique may be that the number of exponential terms used should be equal or greater than the number of biochemical concentrations to be retrieved. Therefore, the larger the number of components assumed to be present in the investigated biological system, the more exponential terms are needed. A large number of decay constants also need to be guessed, potentially making its application difficult. The Laguerre model based method for concentration estimation only requires predefining the Laguerre parameter $\alpha$, which can be chosen from the observed decay data.

All of these findings taken together suggest that the use of the Laguerre expansion method (and specifically, of the expansion coefficients) represent a promising approach for the quantification of relative concentrations of different biochemical compounds in biological systems, and their subsequent characterization and discrimination. Application of Laguerre deconvolution techniques can result not only in accurate analysis of fluorescent systems without a priori knowledge of underlying fluorescence dynamics but also facilitate reduction of data processing time.

Fluorescence Lifetime Imaging Microscopy

Alternate embodiments of the present invention may include a method for analysis of lifetime imaging data. This method may be used to analyze, with accuracy and in real time, compositional and functional changes present in biological samples, either at microscopic and/or macroscopic levels, such as: cell metabolism (e.g., changes in pH, Ca, Mg, oxygen concentration) and the detection of pathologies of specific physiological conditions such as tumors and atherosclerotic plaques.

The Laguerre deconvolution technique is used in this context to produce a robust and extremely fast method for analysis of fluorescence lifetime imaging microscopy data. The method estimates the intrinsic fluorescence decay at every pixel of the image by expanding them on the Laguerre basis. The intrinsic fluorescence decay $h(r,n)$ at every pixel r of the sample image is expressed as:

$$h(r, n) = \sum_{j=0}^{L-1} c_j(r) \cdot b_j^\alpha(n), n = 0, 1, \ldots, S-1 \tag{14}$$

where $c_j(r)$ are the expansion coefficients to be estimated per pixel and contain the time-resolved information of the decays. The method takes advantage of the orthogonality of the Laguerre functions, which implies that the expansion coefficients at every order j are independent from each other, and, therefore, each of them may be estimated separately. Thus, for a given order j, the complete map of expansion coefficients $c_j(r)$ can be estimated in parallel extremely quickly using a common Laguerre basis $b_j^\alpha(n)$ for all of the pixels.

Figure 8:
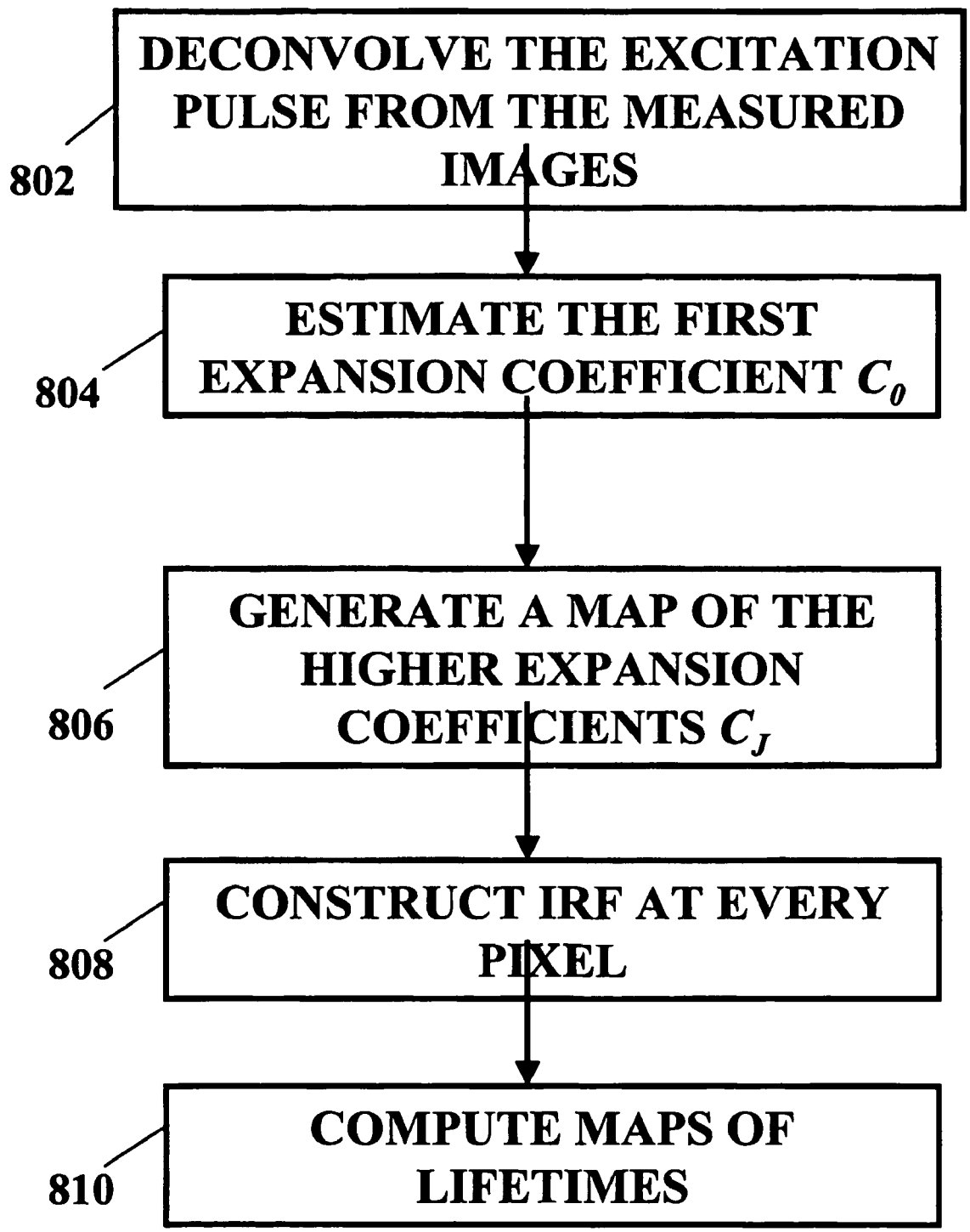
FIG. 8 illustrates a block diagram of a method for analyzing FLIM data according to an embodiment of the present invention.

FIG. 8 further illustrates a method of this embodiment of the present invention. In Block 802, excitation pulse x(n) is deconvolved from the measured images H(r,t) shown below where r denotes the pixel location and t denotes the time gate:

$$H(r, t) = \sum_{j=0}^{L-1} c_j(r) v_j^\alpha(t) \tag{15}$$

$$v_j(n) = T \sum_{j=0}^{M-1} b_j(m) x(n-m)$$

The variable $c_j$ describes the unknown expansion coefficients to be estimated by generalized linear least-square fitting; $v_j(n)$ are the discrete convolutions of the excitation input with the Laguerre functions and denoted as the "key variables"; and L is the number of Laguerre functions used to model the IRF.

As indicated above, the expansion coefficients are independent from each other, and thus may be estimated separately. This condition allows for the reformulation of the computation of the Laguerre expansion coefficients. Considering N delayed images H(r,t) acquired at times $t=(t_1, t_2, \ldots, t_N)$, using an excitation light pulse x(t). The key variables $v_j^\alpha(n)$ can also be resampled at the same times $t=(t_1, t_2, \ldots, t_N)$. Then, the first expansion coefficient can be estimated 804 using the images H(r, t) and the first resampled key variable $v_0^\alpha(n)$, by solving the system of linear equations:

$$H(r,t) = c_0(r) \cdot v_0^\alpha(t), t=t_1, \ldots, t_N \tag{16}$$

Then, by solving $c_0(r)$ from the system of linear equations above using a Least-Square approach, and rewriting the equation in a term-by-term form the following analytical expression is obtained:

$$c_0(r) = \frac{\sum_{k=1}^{N} H(r, t_k) \cdot v_0^\alpha(t_k)}{\sum_{k=1}^{N} (v_0^\alpha(t_k))^2} \tag{17}$$

Taking into consideration that the index r represents a pixel location in the whole image, the previous expression indicates that the complete map of coefficients $c_0(r)$ at each pixel is given simply by the sum of the delayed images H(r,t) weighted by the values at the corresponding time delays, and normalized by the sum of squares of the key variable values $v_0^\alpha(n)$ at all the delay times. Since this operation involves only the sum of N weighted images, its computation time becomes significantly short.

Once the map of the first expansion coefficient $c_0(r)$ is computed, the higher expansion coefficient maps $c_j(r)$ (j=1, \ldots, L-1) can be estimated 806 using a similar approach. Generalizing the method for estimation of the $j^{th}$ expansion coefficient map $c_j(r)$, the N residual images resulting after the estimation of the previous expansion coefficient map can be estimated:

$$H_j(r,t_k)=H_{j-1}(r,t_k)-c_{j-1}(r)\cdot o_{j-1}^\alpha(t_k), k=1,\ldots,N \quad (18)$$

Finally the $j^{th}$ expansion coefficient map $c_j(r)$ is solved by updating equation (17):

$$c_j(r) = \frac{\sum_{k=1}^{N} H_j(r, t_k) \cdot v_j^\alpha(t_k)}{\sum_{k=1}^{N} (v_j^\alpha(t_k))^2} \quad (19)$$

As can be observed, the estimation of the complete maps of the L expansion coefficients only involves sums and subtractions of matrices, which makes the process extremely fast. Once the maps of expansion coefficients are estimated, the intrinsic fluorescence decay $h(r,n)$ at every pixel can be constructed, and the map of lifetimes can then be computed 808 by constructing the IRF at every pixel for S number of time instances:

$$h(r, n) = \sum_{j=0}^{L-1} c_j(r) \cdot b_j^\alpha(n), n = 0, 1, \ldots, S-1 \quad (20)$$

Finally, the lifetime map is computed 810 by interpolating the time point at which the IRF becomes 1/e of its maximum value.

Validation of FLIM Data Analysis

The performance of the FLIM Laguerre deconvolution technique was first tested with synthetic FLIM images generated by a four-exponential model. A total of 600 data sets were generated, yielding average lifetime values between 0.3-12 ns. Then, a series of 600×600 pixel FLIM images were generated, in which each column of the images corresponds to a copy of the 600 multiexponential decays.

Another group of synthetic images were derived from a set of fluorescence lifetime standard dyes, including Rose Bengal (RB), Rhodamin B (RdmB), and 9-cyanoanthracene (9CA). For each dye, 55 time-resolved measurements of the fluorescence decay at the peak emission wavelength were taken. Then, a series of 55×55 pixel FLIM images were generated, in which each column of the images corresponds to a copy of the 55 standard measurements.

Figure 9:
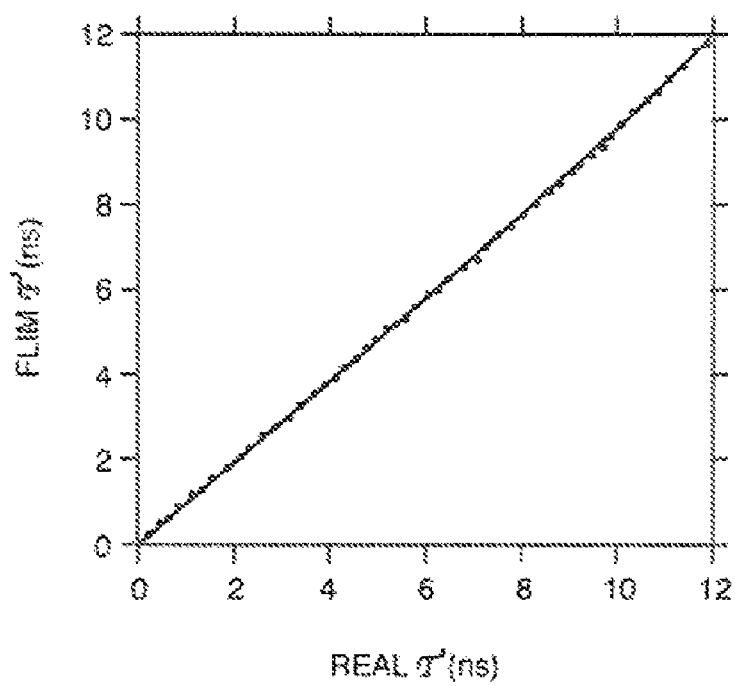
FIG. 9 illustrates a graph comparing real lifetime values to those estimated in accordance with an embodiment of the present invention.

Analysis of the synthetic multiexponential images showed that the FLIM Laguerre deconvolution method was able to retrieve correctly the lifetime map of the synthetic images. As shown in FIG. 9, the lifetime values estimated by our method were very close to the real values, especially for lifetimes above 2 ns. Even more important, it was also observed that the deconvolution of the 600×600 pixel multiexponential images was achieved extremely fast. The complete maps of the Laguerre expansion coefficients $c_j(r)$ were computed in <5 s, and the actual fluorescence IRF at every pixel and the corresponding lifetime map were computed in <20 s. Assuming that conventional FLIM deconvolution methods would perform at 1 ms/pixel, these results would indicate that our method would performs at least 18 times faster.

In order to compare the temporal accuracy of the FLIM Laguerre method against the RLD and the N-RLD methods, lifetime maps of the synthetic images derived from the fluorescence lifetime standard were estimated using the three algorithms. Laguerre deconvolution was performed with 15 and then 5 delayed images, to evaluate the effect of the number of samples in the lifetime estimation. The results of this analysis (mean values of the lifetime maps) are presented in Table 3. The three methods produced lifetime values similar to the ones obtained from the original fluorescence lifetime spectroscopic data (FLS), which were in good agreement with values found in the literature. Fast emitting fluorophores, like RB, with lifetimes ranging in the hundreds of picoseconds were reliably measured by all the methods. Similarly, measurements of RdmB demonstrated the ability of the three methods to accurately resolve nanosecond and subnanosecond fluorescence lifetimes. In order to assess the ability of the algorithms to retrieve long fluorescence lifetimes, measurements of 9/CA in ethanol were also successfully deconvolved. It was also observed that lifetime estimation by the Laguerre method with 15 and 5 delayed images produced similar values.

TABLE 3

Estimated lifetime values of fluorescence standard dyes.

| | Laguerre N = 5(15) | FLIM (ns) RLD | N-RLD | FLS (ns) | Literature | Wavelength (nm) |
|---|---|---|---|---|---|---|
| RB/Eth | 0.74 (0.74) | 0.98 | 0.78 | 0.74 | 0.85 | 590 |
| RdmB/Eth | 2.70 (2.88) | 3.04 | 2.94 | 2.87 | 2.85 | 590 |
| 9-CA/Eth | 11.47 (11.52) | 12.07 | 12.10 | 11.12 | 11.85 | 445 |

Figure 10:
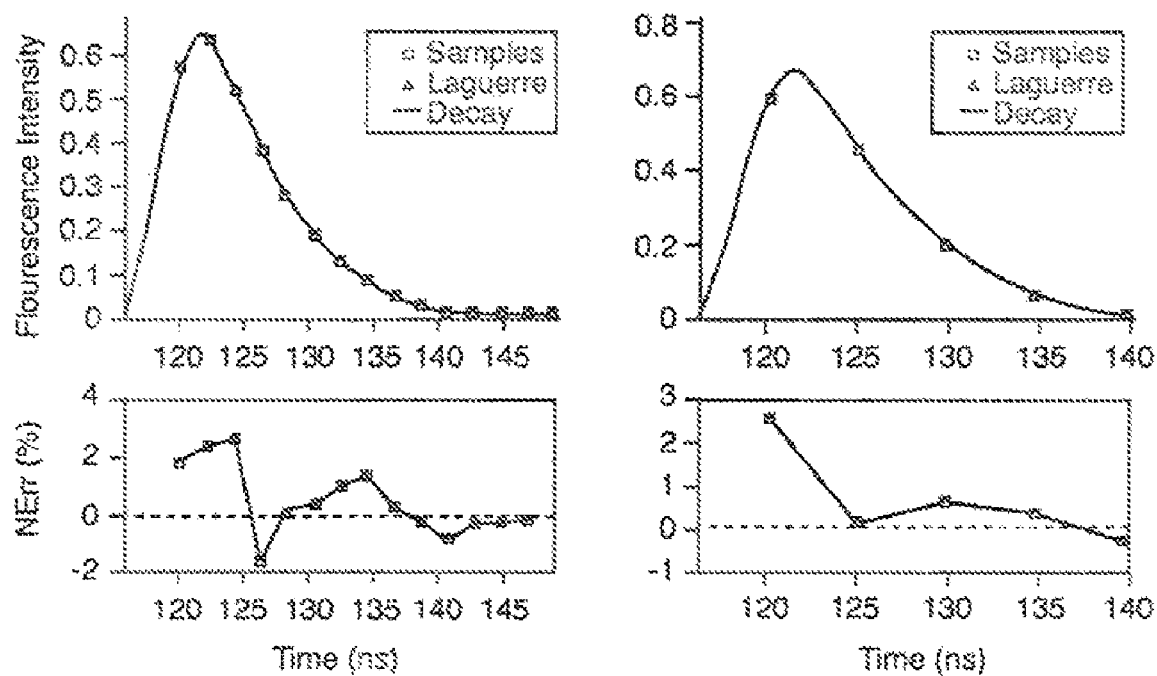
FIG. 10 illustrates a graph of single pixel analysis on a random pixel from RB images using 15 and 5 samples, in accordance with an embodiment of the present invention.

Analysis of the goodness of the fit for the fluorescence decay data from a typical pixel of the synthetic RB images showed very good estimation of the Laguerre deconvolution method. FIG. 10 illustrates the RB pixel decay (solid line), with the samples used for the analysis (squares) and the corresponding Laguerre fit (triangles). The normalized estimation error (NErr) was <4% when either 15 or 5 delayed images were used for deconvolution.

Figure 11:
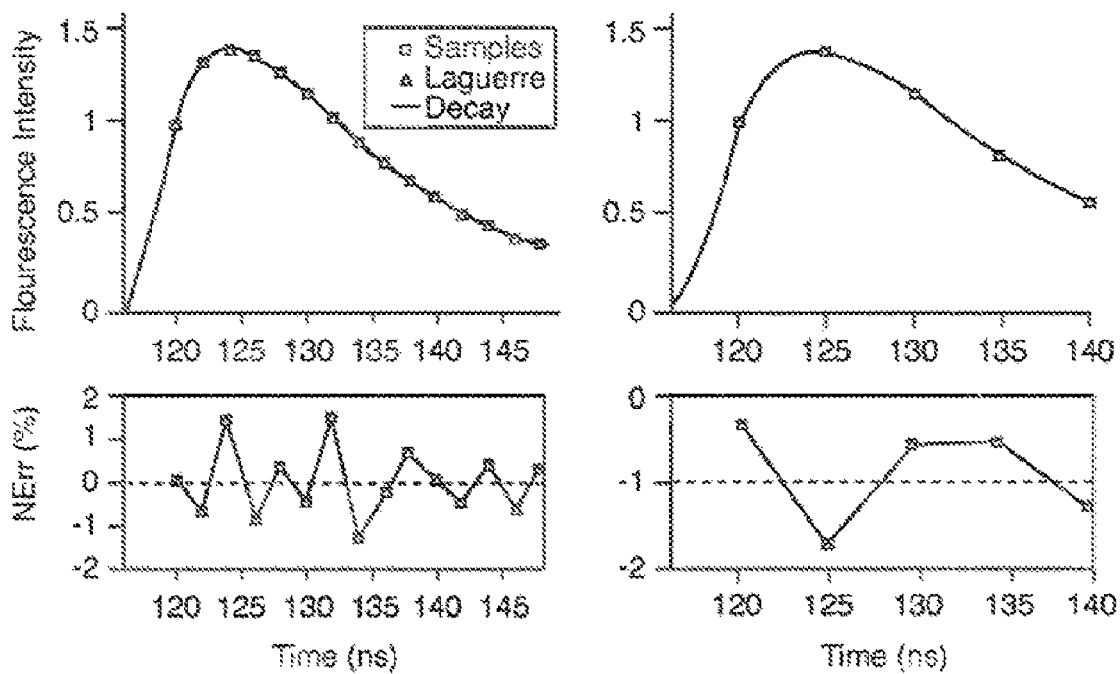
FIG. 11 illustrates a graph of single pixel analysis on a random pixel from RdmB images using 15 and 5 samples, in accordance with an embodiment of the present invention.

Similarly, analysis of the fluorescence decay data from a typical RdmB pixel also showed very good fit, as shown in FIG. 11. For this particular case, the NErr was lower (<0.5%) when only 5 delayed images were analyzed.

Figure 12:
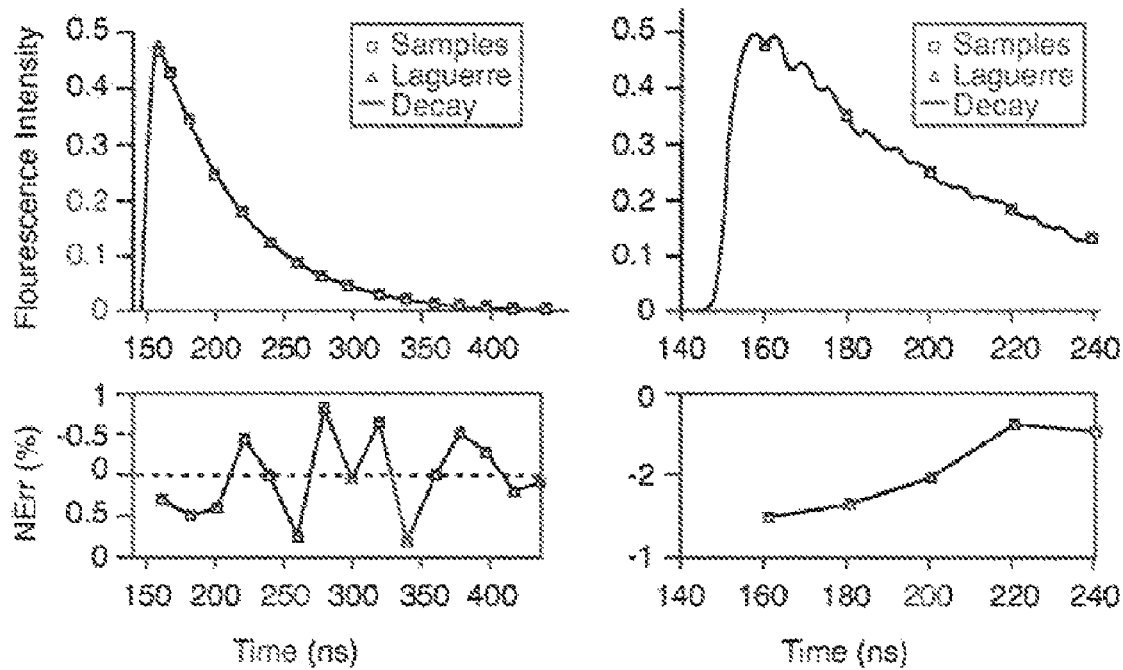
FIG. 12 illustrates a graph of single pixel analysis on a random pixel from 9/CA images using 15 and 5 samples, in accordance with an embodiment of the present invention.

Finally, analysis of the fluorescence decay data from a typical 9/CA pixel also showed very good fit, as shown in FIG. 12. For this case, the NErr was lower (<1%) when 15 delayed images were analyzed.

Accordingly, embodiments of the present invention presents a number of significant advantages over the current algorithms for time-resolved fluorescence imaging: (1) the intrinsic fluorescence intensity decays of any form can be estimated at every pixel as an expansion on a Laguerre basis, without a priori assumption of its functional form; (2) the number of images required to expand the fluorescence IRF from each pixel is relatively low (as low as 5 delayed images), thus allowing the reduction of the acquisition time; (3) ultrafast light sources are not longer required, making less expensive to perform lifetime imaging; (4) finally, and most important, the fluorescence IRF at every pixel is expanded in parallel using a common Laguerre basis, thus reducing significantly the computation time.

All current fast methods of FLIM analysis, such as RLD and N-RLD, estimate maps of lifetime values, which are sufficient to fully characterize the decays at every pixel, if they follow a single exponential dynamic. However, when more complex decay functions need to be considered, other more sophisticated and time-consuming algorithms need to be applied, such as the multiexponential or stretch-exponential methods. The Laguerre FLIM deconvolution technique of an embodiment of the present invention takes advantages of the orthogonality of the Laguerre functions and allows computing the complete maps of expansion coefficients extremely fast. Since the set of expansion coefficients summarize the temporal properties of the IRF that they expand, a complete characterization of the fluorescence decay at every pixel of the image can be achieved in a few seconds.

The results from the simulation of fluorescence lifetime standard images also indicate that accurate estimation of the IRF at every pixel can be achieved with considerably few delayed images. This is of special importance, because standard FLIM deconvolution methods require the acquisition of tens of delayed images. Thus, our method significantly reduces the computation time as well as the acquisition time, since less delayed images needing to be acquired. This would be of special relevance in the context of functional fluorescence lifetime imaging, where real-time acquisition is required.

Finally, most current algorithm of FLIM analysis requires the assumption that the excitation light pulses are negligibly short, so that the fluorescence emission can be approximated to the intrinsic IRF. To accommodate this requirement, most current FLIM system use ultra-fast light sources, which are in general too expensive and sophisticated to be used in real-world applications. Since embodiments of the present invention deconvolve the excitation light pulse from the measured images, excitation with ultra-short pulse is no longer required. Thus, embodiments of the present invention will potentially allow the development of less expensive and complex FLIM system that could be used in a variety of practical applications.

Applications

In numerous fields, including organic chemistry, forensics, medical diagnosis, genetics and molecular biology there is a growing need for safe, efficient and cost-effective methods for identifying compounds of interest within a mixture of compounds. Mixtures of compounds frequently arise as the product of an organic synthetic cycle, during the isolation of a product of biological origin and during the chemical or enzymatic sequencing of polymeric compounds such as polypeptides, proteins, polysaccharides and nucleic acids.

As indicated above, embodiments of the present invention are widely applicable and may be used in a broad range of fields including but not limited to medicine, biology, biochemistry, chemistry, pharmaceutics, and genetics. Since the fluorescence emission of tissue is a composite spectrum of different types of fluorophores, embodiments of the present invention may be used to enhance various applications including but not limited to: microscopic studies of intracellular components and activities; intraoperative identification of a tumor versus normal tissue (e.g., brain tissue, during neurosurgical resection of brain tumors); characterization of the biochemical composition of atherosclerotic plaques, and the identification of predictor markers of plaque rupture; identification of chemicals with biological activity, particularly for automated screening of low volume samples for new drugs discovery; DNA sequencing for the investigation of proteins structures and functions.

The present invention can be implemented on any current fluorescence lifetime imaging microcopy (FLIM) system. Because of its unique advantages, FLIM has become an important optical imaging tool for microscopic studies of intracellular components and activities, and recently for macroscopic tissue level applications. Fluorescence lifetime provide an additional source of contrast to separate multiple fluorophores with overlapping spectra. It is therefore possible to study the location and activities of different intracellular components on the same essay. Moreover, FLIM has been used to imaging locations and dynamics of endogenous fluorophores such as reduced pyridine nucleotides or NAD(p)H and its bonding to proteins. In addition, given sufficient signal-to-noise ratio (SNR), fluorescence lifetime is independent of intensity variation of the excitation light and distribution of the probe. Hence, fluorescence images can provide information about the underlying fluorescence dynamics. Furthermore, fluorescence lifetime is sensitive to the changes in the fluorophores' microenvironment, i.e. pH, temperature, and existence of other chemical species. Therefore, FLIM can be used for quantitative imaging of fluorophore concentrations and dynamics without cumbersome wavelength ratiometric measurements. FLIM has also become an important technique for quantitative measurement of Fröster Resonance Energy Transfer (FRET), which has extensive applications in clinical, biological and biochemical research.

With the anticipated growth in cancer cases as the population ages, the discovery of more effective cancer diagnostic and therapeutics has become critical. There is therefore a concerted effort to commercialize lab tests and instruments, such as the present invention, that have the potential to help physicians to diagnose and monitor cancer patients. One important contribution of the present invention is its ability to distinguish normal from tumor containing tissues found in the human body by simply using the natural fluorescence of tissue. This technology will allow physicians to simply point the TR-LIFS probe at the suspected malignant tissue and based on the probe feedback, determine whether or not the tissue is cancerous/malignant. This will improve the diagnostic accuracy and precision of general surgery, with near term emphasis on brain biopsy. This system allows the physician to make a diagnosis real-time, rather than having to send the tissue sample out to the Pathology Lab and endure the waiting for a sometimes-negative result. These conventional histopahtologic methods are not only time consuming, but also expensive. In addition to being able to make the distinction between different types of tissues, the present invention has the potential to significantly reduce the need of expensive and highly un-necessary biopsies. Considering the cost and risk associated with unguided biopsy, this translates to greater diagnostic accuracy, greater patient comfort, and millions of dollars in savings by the healthcare industry as a whole. In addition, the present invention can be used in conjunction with endoscopes for tissue identification in various types of surgery and can be adapted to a hand held device. The combination of the technical innovation introduced by the present invention with magnitude and fast growth of cancer diagnose market will result in a viable and fast paced product commercialization.

Atherosclerosis is a progressive disease of blood vessels that is reported to be the leading cause of death during middle and late adulthood in economically advanced societies. It has predilection for the critical arterial beds (coronary, cerebral and aortoiliac) and leads to critical events such as myocardial infarction, stroke, and ischemic gangrene of the extremities. Intensive efforts have been made to characterize atherosclerotic lesions in clinical situations. The main task for a technique designed to perform a clinical classification of the lesions is to picture as closely as possible the histological classification which could then be used to accurately determine a treatment for a specific lesion type. Fluorescence spectroscopy-based techniques, including steady-state (spectrally-resolved) and time-resolved approaches, have been shown to detect elastin, collagen, lipids and other sources of autofluorescence in normal and diseased arterial walls as well as to characterize the biochemical composition of atherosclerotic plaques both ex-vivo and in-vivo.

Since the present invention provides a method for estimating the contribution of the three primary fluorophores (elastin, collagen and lipid-rich deposits) in the arterial wall at each clinical stage, atherosclerosis was a prime medical condition with which to apply the method of the present invention to fully characterize atherosclerotic lesions at its varying stages of progression.

The present invention can also be implemented on an automated and integrated system (i.e. multi-well platforms) for rapidly identifying chemicals with biological activity in liquid samples, particularly automated screening of low volume samples for new drugs, agrochemicals, or cosmetics. Systems and methods for rapidly identifying chemicals with biological activity in samples, can benefit a number of different fields. For instance, the agrochemical, pharmaceutical, environmental and cosmetic fields all have applications where large numbers of liquid samples containing chemicals are processed, such as: detecting the presence of an analyte in a sample, and testing a therapeutic for therapeutic activity and toxicology.

DNA sequencing involves determining the order in which the nucleic acid bases are arranged within a length of DNA. Although sequencing and other assay methods that utilize fluorescent markers often represent an improvement over methods that utilize radioactive isotopes, current fluorescent methodologies are hampered by certain deficiencies. For example, in order to identify the individual nucleotides, each nucleotide must bear a fluorescent marker that has by a unique absorbance and/or emission spectrum with a different absorbance or emission maximum. Thus, to clearly distinguish the individual nucleotides based upon the fluorescence spectrum of their tags, the absorbance or emission maxima of each tag must be clearly resolved from those of every other tag. Further, fluorescence must be monitored at a number of different wavelengths in order to detect each of the maxima and a filtering system must be employed. This is cumbersome and increases the expense of the instrumentation. This situation is additionally complicated by the dependence of the absorption or emission maxima for a compound upon the environment surrounding that compound. Thus, a method of detecting individual fluorescently labeled compounds within a mixture of compounds, which relied on a characteristic of the fluorescent lifetime other than its absorption and/or emission spectrum (e.g., maxima) would represent a significant advance in the art. The present invention provides such a method.

While the description above refers to particular embodiments of the present invention, it will be understood that many alternatives, modifications and variations may be made without departing from the spirit thereof. The accompanying claims are intended to embrace such alternatives, modifications and variations as would fall within the true scope and spirit of the present invention. The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A method comprising:
    obtaining a plurality of images of a measured fluorescence intensity decay for a sample having been exposed to an excitation pulse generated by an excitation light source, the measured fluorescence intensity decay being associated with a fluorescence impulse response function;
    deconvolving the excitation pulse from the measured images;
    estimating a first expansion coefficient ($C_0$);
    generating a map of higher expansion coefficients ("$\{c_j\}$");
    expanding the fluorescence impulse response function on a Laguerre basis; and
    computing a map of average lifetimes by constructing an impulse response function ("IRF") at every pixel for a predetermined number of time instances ("S") and interpolating a time point at which the IRF becomes 1/e of its maximum value, wherein the IRF is represented by the equation:

$$h(r, n) = \sum_{j=0}^{L-1} c_j(r) \cdot b_j^\alpha(n), n = 0, 1, \ldots, S - 1.$$

2. The method of claim 1, wherein the sample is selected from the group consisting of a biological tissue, a chemical, a biochemical sample and combinations thereof.

3. The method of claim 1, further including detecting a physiological condition from the group consisting of a tumor and an atherosclerotic plaque.

4. The method of claim 1, further including predicting the distribution of concentration of at least one biochemical component of the sample images, wherein the sample is composed of a plurality of biochemical components.

5. The method of claim 1, further including monitoring an intracellular component and an activity of the intracellular component.

6. The method of claim 1, further including identifying a chemical with a biological activity for automated screening of the sample for new drugs discovery.

7. The method of claim 6, further configured to characterize drugs based on their chemical composition so high speed/throughput surveying and counting of the drugs is possible.

8. The method of claim 6, further configured to characterize a biochemical assay based on biochemical contents to facilitate high speed/throughput surveying/analysis of the assay.

9. The method of claim 1, further including sequencing a deoxyribonucleic acid (DNA) microarray.

* * * * *